(12) United States Patent
Grant

(10) Patent No.: US 11,514,616 B2
(45) Date of Patent: Nov. 29, 2022

(54) AUGMENTED REALITY USING INTRA-OCULAR DEVICES

(71) Applicant: Strathspey Crown, LLC, Newport Beach, CA (US)

(72) Inventor: Robert Edward Grant, Laguna Beach, CA (US)

(73) Assignee: Strathspey Crown, LLC, Newport Beach, CA (US)

( * ) Notice: Subject to any disclaimer, the term of this patent is extended or adjusted under 35 U.S.C. 154(b) by 0 days.

(21) Appl. No.: 17/103,309

(22) Filed: Nov. 24, 2020

(65) Prior Publication Data

US 2022/0164998 A1     May 26, 2022

(51) Int. Cl.
| | | |
|---|---|---|
| G06T 11/00 | (2006.01) | |
| G02B 27/01 | (2006.01) | |
| A61F 2/16 | (2006.01) | |

(52) U.S. Cl.
CPC ............ *G06T 11/00* (2013.01); *A61F 2/16* (2013.01); *G02B 27/0172* (2013.01); *G02B 2027/014* (2013.01); *G02B 2027/0138* (2013.01)

(58) Field of Classification Search
CPC ... G06T 11/00; G06T 19/006; G02B 27/0172; G02B 2027/014; G02B 2027/0138; A61F 2/16; A61F 9/0017; A61F 9/08
See application file for complete search history.

(56) References Cited

U.S. PATENT DOCUMENTS

| | | | |
|---|---|---|---|
| 7,144,423 B2 | 12/2006 | McDonald | |
| 7,229,475 B2 | 6/2007 | Glazier | |
| 9,662,199 B2 | 5/2017 | Grant | |
| 9,916,635 B2 | 3/2018 | Kim | |
| 9,995,936 B1 | 6/2018 | Macannuco et al. | |
| 10,467,992 B2 | 11/2019 | Deering | |
| 2009/0278937 A1* | 11/2009 | Botchen | G06K 9/00771 348/169 |
| 2013/0044042 A1 | 2/2013 | Olsson et al. | |
| 2015/0036221 A1 | 2/2015 | Stephenson | |

(Continued)

FOREIGN PATENT DOCUMENTS

| | | |
|---|---|---|
| CN | 110955063 | 4/2020 |
| CN | 110955063 A * | 4/2020 |

(Continued)

OTHER PUBLICATIONS

International search report dated Mar. 17, 2022, for related PCT application No. PCT/US2021/060841. 3 pages.

*Primary Examiner* — Jeffery A Brier

(74) *Attorney, Agent, or Firm* — Fish IP Law, LLP

(57) ABSTRACT

In a system for providing augmented reality to a person disposed in a real-world, physical environment, a camera is configured to capture multiple real-world images of a physical environment. The system includes a processor configured to use the real-world images to generate multiple images of a virtual object that correspond to the multiple real-world images. The system further includes a display configured to display to the person in real time, a succession of the generated images that correspond to then-current multiple real-world images, such that the person perceives the virtual object to be positioned within the physical environment.

15 Claims, 6 Drawing Sheets

(56) References Cited

U.S. PATENT DOCUMENTS

| | | | |
|---|---|---|---|
| 2015/0049004 A1* | 2/2015 | Deering | G02B 27/0172 |
| | | | 345/8 |
| 2015/0182330 A1* | 7/2015 | Grant | A61B 5/1112 |
| | | | 623/6.37 |
| 2016/0109713 A1 | 4/2016 | Osterhout | |
| 2016/0350973 A1* | 12/2016 | Shapira | G06F 3/017 |
| 2017/0075414 A1* | 3/2017 | Grant | G06F 3/011 |
| 2020/0020308 A1 | 1/2020 | Deering et al. | |
| 2020/0043239 A1 | 2/2020 | Lee | |
| 2020/0118337 A1* | 4/2020 | Yeung | G06T 17/05 |
| 2020/0307616 A1* | 10/2020 | Nithiyanantham | B60K 35/00 |

FOREIGN PATENT DOCUMENTS

| | | |
|---|---|---|
| KR | 101895085 | 2/2015 |
| WO | 2020107127 | 6/2020 |

\* cited by examiner

AUGMENTED REALITY USING INTRA-OCULAR DEVICES

FIELD OF THE INVENTION

The field of the invention is augmented reality systems coupled and/or integrated with a human body.

BACKGROUND

The inventive concepts herein aim to execute augmented reality imaging and rendering tasks using a variety of analytical techniques, including artificial intelligence-based technologies, to identify one or more elements in the environment and provide information and augmentations to the environment.

Specifically, the present invention provides a system of using a display device, such as an intraocular display, to augment the local environment.

In conventional systems, augmented reality systems use devices that are substantially separated from the body to provide the means of processing data associated with the local environment and displaying augmentations to the local environment based on the processed data. The presently claimed invention enables augmented-reality environments to be delivered via devices integrated into the human body, such as intraocular lenses. By integrating augmented reality into intraocular lenses and other integrated human-machine systems, the invention herein is not only available to display an accurate representation of the surrounding physical environment, but further enhance the environment with visual and non-visual features that provide an enhanced representation. For example, augmented reality-enabled intraocular devices can use intraocular displays to enhance certain colors or provide information beyond the reach of the sensory limitations of human (e.g., visual highlights derived from a coupled infrared camera in low-light situations).

U.S. Pat. No. 9,995,936 B2 to Macannuco teaches the overlaying of an infrared portion of a live scene using a head-mounted display. The head-mounted display overlays a virtual image on to the infrared portion. Macannuco described extraocular display elements used to deliver infrared lighting and virtual overlays. As such, Macannuco fails to contemplate the integration of visually augmenting the environment using an intraocular display that is not limited to overlaying images onto infrared emitting portions of a user's environment.

U.S. Pat. No. 10,467,992 to Deering teaches an intraocular display technology using femto projectors to project light onto the retina to send an image to the user's brain. However, Deering fails to contemplate the use of variable opacity, the types of sensors and augmentations coupled to the present invention, and/or the hybridization of a stereoscopic image and a real-world image.

Macannuco, Deering, and all other extrinsic materials discussed herein are incorporated by reference to the same extent as if each individual extrinsic material was specifically and individually indicated to be incorporated by reference. Where a definition or use of a term in an incorporated reference is inconsistent or contrary to the definition of that term provided herein, the definition of that term provided herein applies and the definition of that term in the reference does not apply.

Thus, there is still a need for processing systems that can process and manipulate environmental data using from one or more sensors and display an enhanced environment beyond conventional human limitations using intraocular displays.

SUMMARY OF THE INVENTION

The inventive concept herein contemplates a system for providing augmented reality to a person disposed in a real-world, physical environment.

The system includes a camera, a processor, and a display. The camera is configured to capture multiple real-world images of a physical environment. The processor is configured to use the real-world images to generate multiple images of a virtual object that correspond to the multiple real-world images. The display is configured to display to the person in real time, a succession of the generated images that correspond to then-current multiple real-world images, such that the person perceives the virtual object to be positioned within the physical environment.

Various resources, features, aspects and advantages of the inventive subject matter will become more apparent from the following detailed description of preferred embodiments, along with the accompanying drawing figures in which like numerals represent like components.

DETAILED DESCRIPTION

It should be noted that while the following description is drawn to a computer-based scheduling system, various alternative configurations are also deemed suitable and may employ various computing devices including servers, interfaces, systems, databases, engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclose apparatus. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network.

One should appreciate that the disclosed techniques provide many advantageous technical effects including allowing users to access augmented reality environments. Augmented reality environments can include any combination of virtual and augmented reality environments and/or environmental elements.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

Figure 1:
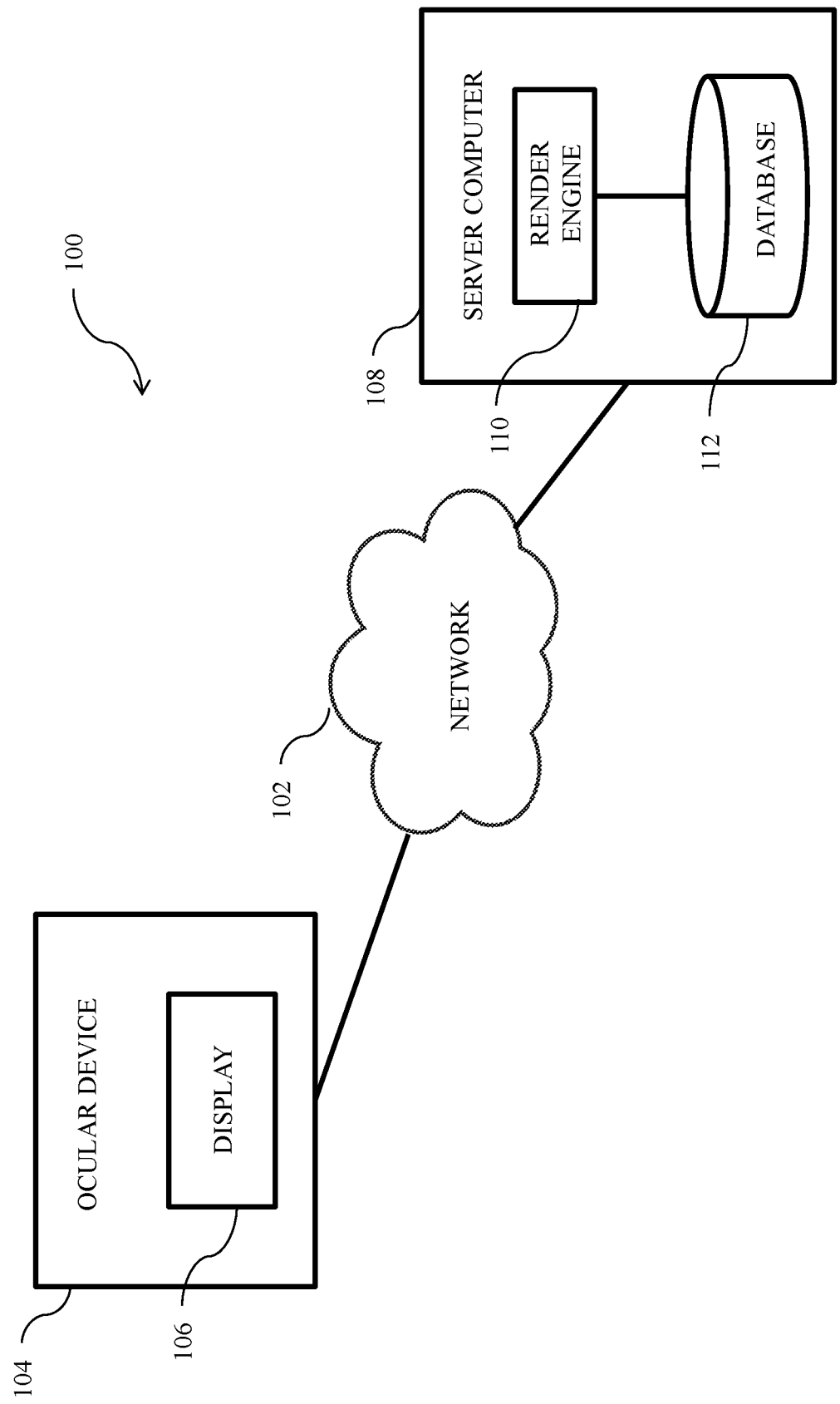
FIG. 1 is a functional block diagram illustrating a distributed data processing environment.

FIG. 1 is a functional block diagram illustrating a distributed data processing environment.

The term "distributed" as used herein describes a computer system that includes multiple, physically distinct devices that operate together as a single computer system. FIG. 1 provides only an illustration of one implementation and does not imply any limitations with regard to the environments in which different embodiments may be implemented. Many modifications to the depicted environment may be made by those skilled in the art without departing from the scope of the invention as recited by the claims.

Distributed data processing environment 100 includes ocular device 104 and server computer 108, interconnected over network 102. Network 102 can include, for example, a telecommunications network, a local area network (LAN), a wide area network (WAN), such as the Internet, or a combination of the three, and can include wired, wireless, or fiber optic connections. Network 102 can include one or more wired and/or wireless networks that are capable of receiving and transmitting data, voice, and/or video signals, including multimedia signals that include voice, data, and video information. In general, network 102 can be any combination of connections and protocols that will support communications between ocular device 104, server computer 108, and any other computing devices (not shown) within distributed data processing environment 100.

It is contemplated that ocular device 104 can be any programmable electronic computing device capable of communicating with various components and devices within distributed data processing environment 100, via network 102. It is further contemplated that ocular device 104 can execute machine readable program instructions and communicate with any devices capable of communication wirelessly and/or through a wired connection. Ocular device 104 includes an instance of ocular display 106.

Ocular display 106 provides a display output coupled to render engine 110. Preferably, ocular display 106 comprises a graphical user interface (GUI) or a web user interface (WUI) that can display one or more of text, documents, web browser windows, user option, application interfaces, and operational instructions. It is also contemplated that user interface can include information, such as, for example, graphics, texts, and sounds that a program presents to a user and the control sequences that allow a user to control a program.

In some embodiments, user interface can be mobile application software. Mobile application software, or an "app," is a computer program designed to run on smart phones, tablet computers, and any other mobile devices.

In some embodiments, ocular display 106 can be configured to substantially mimic the field of view and other the optical characteristics of a human eye. For example, ocular display 106 may use Fresnel lenses to render a stereoscopically accurate overlay. In another example, ocular display 106 may use an aspherical lens to render a stereoscopically accurate overlay. In other embodiments, ocular display 106 can be directly integrated into a lens to display one or more graphical elements. For example, ocular display 106 can be integrated into a lens replacement, such as an intraocular lens replacement.

In other embodiments, ocular display 106 can be a separate element placed within the surface of the eyeball. For example, ocular display 106 can be sized and positioned to reside between the iris and the cornea of a human eyeball.

It is contemplated that ocular display 106 can be configured to have variable opacity in order to allow ocular display 106 to switch from a substantially transparent configuration to a substantially opaque configuration. It is also contemplated that the variable opacity can also have a limited range anywhere between the substantially transparent configuration and the substantially opaque configuration.

In some embodiments, ocular display 106 can selectively control the opacity. For example, ocular display 106 can limit transparency to a certain portion of ocular display 106 to highlight the most relevant points of focus. In another example, ocular display 106 can limit transparency to certain portions of ocular display 106 to control how light passes through to the retina of the eyeball.

The present invention contemplates any means of changing the transparency of a display. For example, ocular display 106 can be configured to alter the transparency of the display when exposed to an electrical current and/or magnetic field incident to the display. In another example, display 106 can be configured to alter the transparency of the display using a first polarized lens and a second polarized lens. By altering the position of the first polarized lens relative to the second polarized lens, ocular display 106 can control the amount of light able to pass through the lens array.

Server computer 108 can be a standalone computing device, a management server, a web server, a mobile computing device, or any other computing system capable of receiving, sending, and processing data.

It is contemplated that server computer 108 can include a server computing system that utilizes multiple computers as a server system, such as, for example, a cloud computing system.

In other embodiments, server computer 108 can be a computer system utilizing clustered computers and components that act as a single pool of seamless resources when accessed within distributed data processing environment 100.

Database 112 is a repository for data used by render engine 110. In the depicted embodiment, render engine 110 resides on server computer 108. However, database 112 can reside anywhere within a distributed data processing environment provided that render engine 110 has access to database 112.

Data storage can be implemented with any type of data storage device capable of storing data and configuration files that can be accessed and utilized by server computer 108. Data storage devices can include, but are not limited to, database servers, hard disk drives, flash memory, and any combination thereof.

Figure 2:
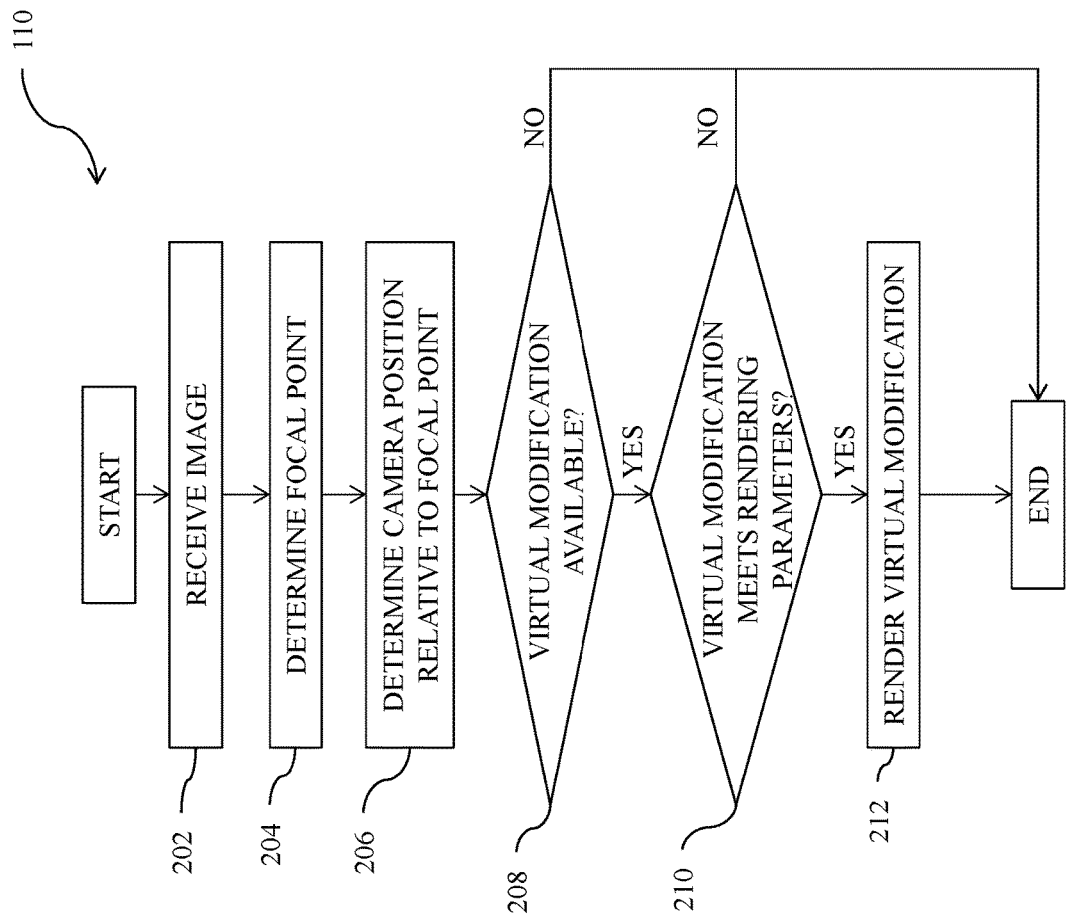
FIG. 2 is a schematic of a method of rendering an image to an intraocular display, such as ocular display 106.

FIG. 2 is a schematic of a method of rendering an image to an intraocular display, such as ocular display 106.

Render engine 110 receives an image (step 202).

Images can be sourced from any sensors associated with ocular device 104. In some embodiments, the sensors are separated from ocular device 104 and ocular display 106. For example, the sensors can include a separate camera that receives visual data from the environment. In a related example, the sensors can include cameras that detect light waves outside of the visible frequencies for humans.

In another example, the sensors can include a spatial sensor operatively coupled to a computer processor, ocular device 104, and ocular display 106.

In other embodiments, the sensors can be configured to sense non-visual data. For example, the sensors can include a sound sensor to capture sounds outside the frequency range of human hearing. In another example, the sensors can include a chemical sensor to detect chemicals in the environment. In another example, the sensors can include a microbial sensors to detect microbes in the environment. In yet another example, the sensors can include an electrical sensor to detect physiological changes in a human body.

In yet other embodiments, the sensors can include supplementary devices to enhance the accuracy of detecting environmental elements. For example, a sensor array can include a device configured to emit electromagnetic energy to be detected by an electromagnetic sensor.

Render engine 110 determines a focal point (step 204).

Render engine 110 can determine a focal point using any one or more analytical techniques.

In one embodiment, render engine 110 can source eye-tracking data from ocular device 104. For example, ocular device 104 can include tracking componentry that determines the position of a point corresponding to a user's line of sight relative to the eye socket. To further this example, render engine 110 can determine the position of the center point of ocular display 106, which corresponds to the center of a user's pupil. In another example, eye tracking can be determined by comparing multiple intraocular positioning sensors positioned in a line that is substantially centered and substantially parallel to the direction of the user's focus.

In a related example, eye tracking data can be sourced from externally coupled sensors. For example, an eye-tracking camera coupled to a computer processor executing program instructions to extract focal point data can be used to determine where a user is looking. In a more specific example, render engine 110 can source focal point data using a human-machine interface that measures the reflection of infrared light beams from a user's eyeball to determine the position of the user's pupil and corresponding focal point.

Render engine 110 determines a position of a camera relative to a focal point (step 206).

Cameras, such as external camera 402 discussed in further detail below, can include any one or more sensors that collect visual and spatial data. In one embodiment, the camera can be positioned outside of the user's body. In such embodiments, render engine 110 manages the correlation of the imaging from the camera to the focus of a user. For example, render engine 110 can determine the vertical, horizontal, and rotational offset (e.g., six degrees of freedom) of the camera and cause one or more processors to correct the offset and align with a user's focus.

In alternative embodiments, the camera is sized for direct integration into the eyeball. For example, a camera can be sized to fit between the lens of an eyeball and the cornea in order to more closely align with the user's focal direction.

Render engine 110 determines whether a virtual modification is available (decision block 208).

Render engine 110 can determine whether a virtual modification using any one or more analytical techniques. For example, analytical techniques can include conventional algorithms. In other examples, analytical techniques can include non-traditional algorithms, such as machine learning algorithms and other predictive analytical techniques. It is further contemplated that any combination of traditional and non-traditional algorithms can be used cooperatively to process any one or more data sources.

In one embodiment, render engine 110 determines whether a virtual modification is available using a traditional algorithm. For example, render engine 110 can extract visual feature data from an image, determine a composite score, compare the visual feature data to data within an object recognition databank, and determine which objects fit the original image most closely. Based on the recognized environmental features, render engine 110 may determine one or more available virtual modifications.

In a related embodiment, render engine 110 determines whether a virtual modification is available using a combination of traditional algorithms and machine learning algorithms. Similarly to the preceding traditional algorithm example, render engine 110 can extract visual feature data from an image, compare the visual feature data to data within an object recognition databank, and determine which objects fit the original image most closely. However, the object recognition databank can be further coupled to a set of program instructions configured to continue adding image data and analyzing the added image data using one or more machine learning algorithms. Based on the recognized environment features, render engine 110 may determine one or more available virtual modifications.

For example, render engine 110 can use a supervised learning classifier analyze an image of a chair in a store and determine a composite score indicating the similarity of the images to one or more pre-loaded images of chairs. Based on the composite score being within a similarity threshold to the other images in the object recognition databank, render engine 110 can add the image of the chair and associated data to the object recognition databank In a related example, render engine 110 can further determine the relationship of the chair and the store environment to historical user data to determine, using a linear regression analysis, predict user intent in directing focus to a particular chair, such as the intent to purchase the product or the intent to sit on the chair.

Responsive to determining that the virtual modification is available ("YES" branch, decision block 208), render engine 110 determines whether the virtual modification meets a rendering parameter (decision block 210).

Rendering parameters can include any one or more variable weighed to determine whether to render a visual element and, if so, how to render to the visual element. In some embodiments, the one or more variables are weighed to determine a composite rendering score. For example, rendering parameters can determine whether user historical data indicates a preference for visual environmental augmentation in a particular environment, such as whether or not a user will prefer subtitles to be rendered and overlaid over a movie screen in a dark movie theater.

In another embodiment, rendering parameters can include binary variables. For example, rendering parameters can limit certain types of visual augmentations from occurring in particular geolocations, such as advertisements inside of a family home. In another embodiment, rendering parameters can limit certain types of visual augmentations based on user characteristic data. For example, render engine 110 can restrict visual augmentations that include mature references based on the age of a user.

Responsive to determining that the virtual modification does not meet the rendering parameter ("NO" branch, decision block 208), render engine 110 ends.

Responsive to determining that the virtual modification meets the rendering parameter ("YES" branch, decision block 210), render engine 110 renders the virtual modification (step 212).

Render engine 110 can render the visual modification in any manner available in the art. In some embodiments, render engine 110 augments an existing environmental feature. For example, render engine 110 can make the sign of a restaurant glow brighter to indicate final destination of a user. In another example, render engine 110 can adjust the coloration of existing objects to accommodate color-blindness limitations and accurately display colors to a user. In yet another example, render engine 110 can change the color of the floor to red to indicate the path towards an emergency exit.

In other embodiments, render engine 110 renders a unique visual element that is indirectly tied to the existing environment. For example, render engine 110 can render visuals and text that provide additional information about particular individuals during a networking event. In another example, render engine 110 can render virtual decorations associated with a birthday party when inside a particular geolocation during a predetermined time interval.

Responsive to determining that the virtual modification does not meet the rendering parameter ("NO" branch, decision block 210), render engine 110 ends.

Figure 3C:
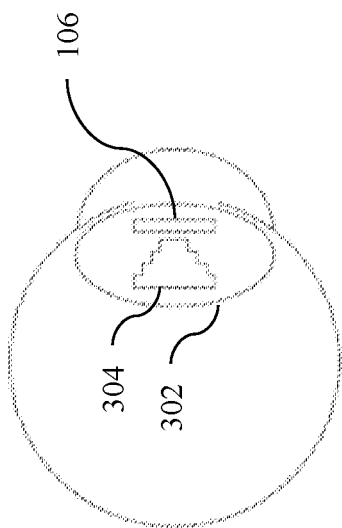
FIGS. 3A-3C depict illustrative embodiments showing how a display and other optical componentry can be integrated into the human eye.
Figure 3B:
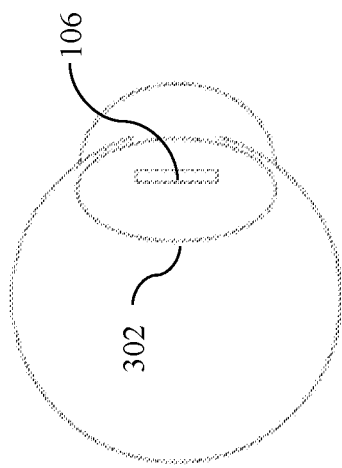
Figure 3A:
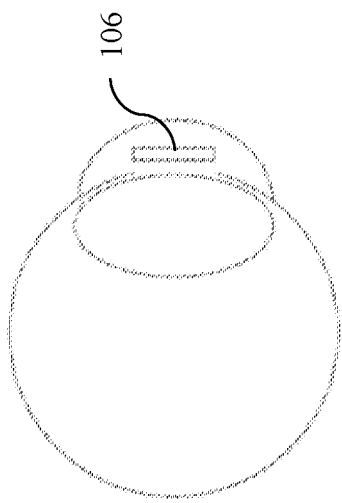

FIGS. 3A-3C depict illustrative embodiments of how ocular device 104 and ocular display 106 can be integrated into the human eyeball. However, the present invention can be applied to extracorporeal devices, such as over-eye embodiments. Additionally, the present invention can be applied to hybrid-systems using a mixture of extracorporeal devices and bio-integrated devices.

FIG. 3A depicts an embodiment in which ocular display 106 is installed between the cornea and the iris of the eye. Ocular display 106 is configured to display modified images adapted to display the correct final image when light associated with the modified image passes to through the lens of the eyeball.

FIG. 3B depicts an embodiment in which ocular display 106 is installed within lens 302. Lens 302 can be made of organic materials, such as the natural human lens, or synthetic, such as a lens implant.

It is contemplated that ocular display 106 can be configured to have variable opacity in order to allow ocular display 106 to switch from a substantially transparent configuration to a substantially opaque configuration. It is also contemplated that the variable opacity can also have a limited range anywhere between the substantially transparent configuration and the substantially opaque configuration.

In some embodiments, ocular display 106 can selectively control the opacity. For example, ocular display 106 can limit transparency to a certain portion of ocular display 106 to highlight the most relevant points of focus. In another example, ocular display 106 can limit transparency to certain portions of ocular display 106 to control how light passes through to the retina of the eyeball.

FIG. 3C depicts an alternative embodiment in which ocular display 106 is installed within lens 302 with optics 304 to product a stereoscopically accurate image. For example, optics 304 can be an aspherical lens configured to alter the light emitted from the display to the retina, such that an intended visual representation is sent to a user's brain. In another example, optics 304 can be a Fresnel lens configured to alter the light emitted from the display to the retina, such that an intended visual representation is sent to a user's brain. However, optics 304 can include any one or more components configured to additionally alter the characteristics of light hitting the retina to convey an intended visual effect. Producing a stereoscopically accurate image is contemplated to be especially important in embodiments where ocular display 106 is bio-integrated into one eye of a paired set of eyes. The present invention contemplates combining the real-world perspective with the augmentations provided, in part, via ocular display 106. By ensuring stereoscopic accuracy, the present invention overcomes issues associated with focusing issue associated with having a display in close proximity to the retina and naturally integrating the image of the display with the unfiltered vision of the second eye.

Figure 4:
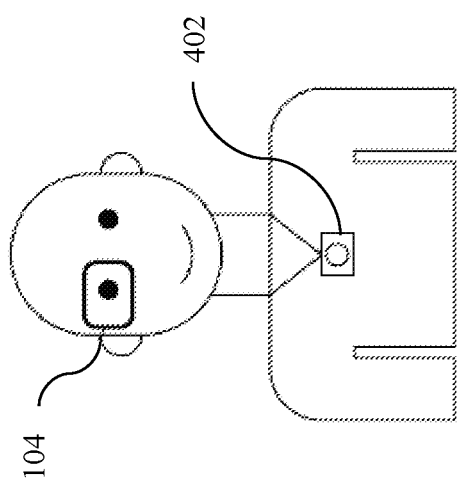
FIG. 4 depicts an anterior view of a user using an ocular device and wearing external camera.

FIG. 4 depicts an anterior view of a user using ocular device 104 and wearing external camera 402. External camera 402 can include any one or more imaging devices and image processing devices configured to capture an environment about the user.

Figure 5:
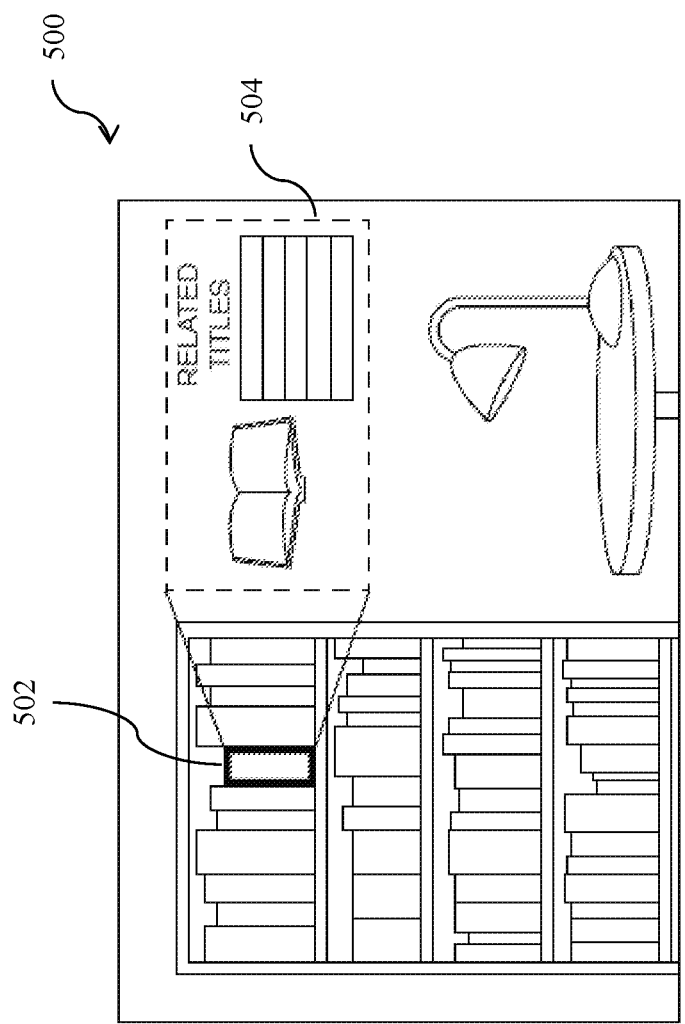
FIG. 5 depicts an exemplary environment, which includes an object associated with an augmentation.

FIG. 5 depicts exemplary environment 500, which includes object 502 associated with augmentation 504. In the depicted embodiment, object 502 is highlighted to increase the appearance of object 502 in the brain of the user. For example, object 502 can be outlined, color shifted, enlarged, and/or subject to any other visual augmentation differentiating the appearance of object 502 from other environment features.

Augmentation 504 can include any additional information sent to the user's brain via the retina. In the depicted embodiment, augmentation 504 can include information that is rendered and displayed to a user.

Figure 6:
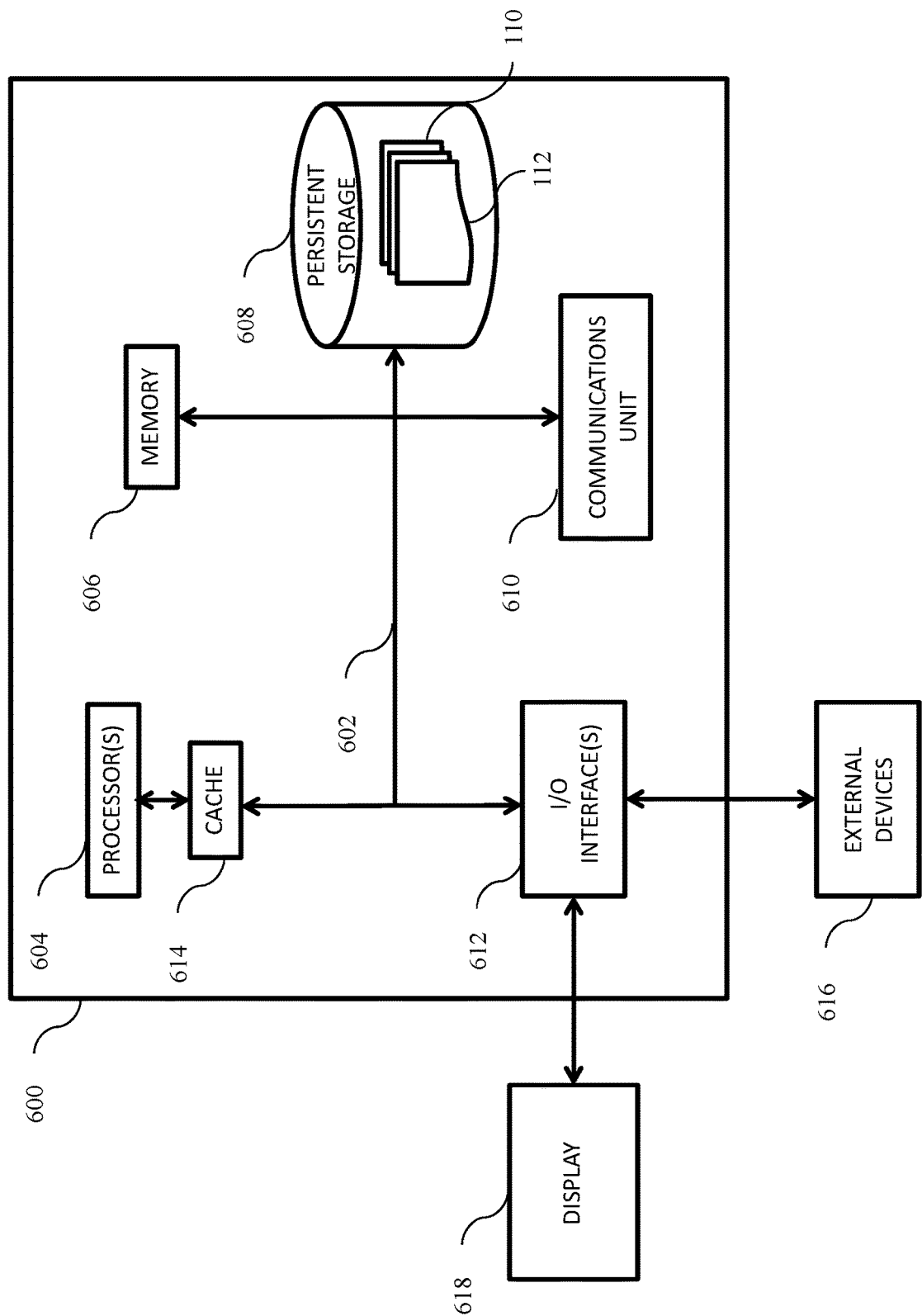
FIG. 6 depicts a block diagram of components of the server computer executing the render engine within the distributed data processing environment of FIG. 1.

FIG. 6 depicts a block diagram of components of the server computer executing the render engine 110 within the distributed data processing environment of FIG. 1. FIG. 6 is not limited to the depicted embodiment. Any modification known in the art can be made to the depicted embodiment.

In one embodiment, the computer includes processor(s) 604, cache 614, memory 606, persistent storage 608, communications unit 610, input/output (I/O) interface(s) 612, and communications fabric 602.

Communications fabric 602 provides a communication medium between cache 614, memory 606, persistent storage 608, communications unit 610, and I/O interface 612. Communications fabric 602 can include any means of moving data and/or control information between computer processors, system memory, peripheral devices, and any other hardware components.

Memory 606 and persistent storage 608 are computer readable storage media. As depicted, memory 606 can include any volatile or non-volatile computer storage media. For example, volatile memory can include dynamic random-access memory and/or static random-access memory. In another example, non-volatile memory can include hard disk drives, solid state drives, semiconductor storage devices, a read-only memory (ROM), an erasable programmable read-only memory (EPROM), a flash memory, and any other storage medium that does not require a constant source of power to retain data.

In one embodiment, memory 606 and persistent storage 608 are random access memory and a hard drive hardwired to computing device 604, respectively. For example, computing device 604 can be a computer executing the program instructions of render engine 110 communicatively coupled to a solid-state drive and DRAM.

In some embodiments, persistent storage 608 is removable. For example, persistent storage 608 can be a thumb drive or a card with embedded integrated circuits.

Communications unit 610 provides a medium for communicating with other data processing systems or devices, including data resources used by ocular device 104. For example, communications unit 610 can comprise multiple network interface cards. In another example, communications unit 610 can comprise physical and/or wireless communication links.

It is contemplated that render engine 110, database 112, and any other programs can be downloaded to persistent storage 408 using communications unit 610.

In a preferred embodiment, communications unit 610 comprises a global positioning satellite (GPS) device, a cellular data network communications device, and short to intermediate distance communications device (e.g., Bluetooth °, near-field communications, etc.). It is contemplated that communications unit 610 allows ocular device 104 to communicate with other computing devices 104 associated with other users.

Display 618 is contemplated to provide a mechanism to display information from render engine 110 through ocular device 104. In preferred embodiments, display 618 can have additional functionalities. For example, display 618 can be a pressure-based touch screen or a capacitive touch screen.

In yet other embodiments, display 618 can be any combination of sensory output devices, such as, for example, a speaker that communicates information to a user and/or a vibration/haptic feedback mechanism. For example, display 618 can be a combination of a touchscreen in the dashboard of a car, a voice command-based communication system, and a vibrating bracelet worn by a user to communicate information through a series of vibrations.

It is contemplated that display 618 does not need to be physically hardwired components and can, instead, be a collection of different devices that cooperatively communicate information to a user.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models. The characteristics are as follows: on-demand self-service: a cloud consumer can unilaterally provision computing capabilities, such as server time and network storage, as needed automatically without requiring human interaction with the service's provider. Broad network access: capabilities are available over a network and accessed through standard mechanisms that promote use by heterogeneous thin or thick client platforms (e.g., mobile phones, laptops, and PDAs). Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a high level of abstraction (e.g., country, state, or data center). Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time. Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider Service Models are as follows: Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings. Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations. Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of selected networking components (e.g., host firewalls).

Deployment Models are as follows: Private cloud: the cloud infrastructure is operated solely for an organization. It may be managed by the organization or a third party and may exist on-premises or off-premises. Community cloud: the cloud infrastructure is shared by several organizations and supports a specific community that has shared concerns (e.g., mission, security requirements, policy, and compliance considerations). It may be managed by the organizations or a third party and may exist on-premises or off-premises. Public cloud: the cloud infrastructure is made available to the general public or a large industry group and is owned by an organization selling cloud services. Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product. The computer program product may include a computer readable storage medium (or media) having computer readable program instructions thereon for causing a processor to carry out aspects of the present invention.

The computer readable storage medium can be any tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, a special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, a segment, or a portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A system for providing augmented reality to a person disposed in a real-world, physical environment, comprising:
   a camera configured to capture multiple real-world images of a physical environment, wherein the camera is capable of detecting light waves in a frequency outside human visual range;
   a processor configured to use the real-world images to generate multiple images of a virtual object that correspond to the multiple real-world images, including a representation of the detected light waves that is within the human visual range;
   a display configured to display to a first eye of the person in real time, composite images of both the generated images including the representation of the detected light waves and the corresponding then current real-world images, such that the person perceives the virtual object to be positioned within the physical environment;
   wherein the display is a component in an intra-ocular device positioned within the first eye, and the display is configured to substantially occlude from the first eye, vision of the physical environment, while displaying the composite images.

2. The system of claim 1, wherein the processor is configured to cause the display to substantially occlude from the first eye the vision of the physical environment by controlling a signal configured to alter transparency of the display.

3. The system of claim 2, wherein the processor is configured to alter transparency of the display by altering an electrical current or magnetic field incident to the display.

4. The system of claim 2, wherein the processor is configured to alter transparency of the display by rotating a first polarization grid relative to a second polarization grid.

5. The system of claim 1, wherein the camera is a component of the intra-ocular device.

6. The system of claim 1, wherein the camera is positioned exterior to the person.

7. The system of claim 1, further comprising a sensor other than the camera, and the processor includes within at least some of the generated images, a representation of information sensed by the sensor.

8. The system of claim 7, wherein the sensor is configured to sense light waves in a frequency outside human visual range.

9. The system of claim 7, wherein the sensor is configured to sense sounds in a frequency outside human auditory range.

10. The system of claim 9, wherein the sensor is configured to sense a physiological state of the person.

11. The system of claim 7, wherein the sensor is configured to sense a chemical composition.

12. The system of claim 7, wherein the sensor is configured to sense a microbe.

13. The system of claim 1, further comprising a sensor configured to sense electromagnetic energy and an emitter configured to emit electromagnetic energy in a frequency that can be detected by the sensor.

14. The system of claim 1, further comprising an electronic circuit configured to transmit the composite of the succession of the generated images and the corresponding then current multiple real-world images.

15. The system of claim 1, wherein the intra-ocular device positioned within the first eye comprises the intra-ocular device positioned within:
   the lens of the first eye; or
   between the cornea and the iris of the first eye.

* * * * *